(12) United States Patent
Puusaari et al.

(10) Patent No.: US 7,474,730 B2
(45) Date of Patent: Jan. 6, 2009

(54) COMPENSATION FOR FLUCTUATIONS OVER TIME IN THE RADIATION CHARACTERISTICS OF THE X-RAY SOURCE IN AN XRF ANALYSER

(75) Inventors: Erkki Tapani Puusaari, Espoo (FI); Oleg Shirokobrod, Helsinki (FI)

(73) Assignee: Oxford Instruments Analytical OY, Espoo (FI)

( * ) Notice: Subject to any disclaimer, the term of this patent is extended or adjusted under 35 U.S.C. 154(b) by 75 days.

(21) Appl. No.: 11/581,929

(22) Filed: Oct. 17, 2006

(65) Prior Publication Data

US 2008/0095309 A1    Apr. 24, 2008

(51) Int. Cl.
*G01N 23/223* (2006.01)
*G01T 1/40* (2006.01)
(52) U.S. Cl. .................. 378/48; 378/161; 378/207
(58) Field of Classification Search .............. 378/48, 378/161, 207
See application file for complete search history.

(56) References Cited

U.S. PATENT DOCUMENTS

| | | | |
|---|---|---|---|
| 2,241,432 A | | 5/1941 | Von Ardenne et al. |
| 3,262,002 A | | 7/1966 | Kreplin |
| 3,319,064 A | | 5/1967 | Guernet et al. |
| 3,409,769 A | * | 11/1968 | McKinney et al. ............. 378/47 |
| 3,462,598 A | * | 8/1969 | Burke et al. ................... 378/47 |
| 4,016,419 A | * | 4/1977 | Kotani et al. .................. 378/48 |
| 4,061,944 A | | 12/1977 | Gay |
| 4,119,234 A | | 10/1978 | Kotschak |
| 4,362,935 A | | 12/1982 | Clark, III |
| 4,577,338 A | | 3/1986 | Takahashi et al. |
| 4,928,293 A | * | 5/1990 | Behncke ....................... 378/50 |
| 4,962,517 A | * | 10/1990 | Koga ............................ 378/48 |
| 5,039,203 A | | 8/1991 | Nishikawa |

(Continued)

FOREIGN PATENT DOCUMENTS

JP    2-24545    1/1990

(Continued)

OTHER PUBLICATIONS

U.S. Appl. No. 11/281,638, filed Nov. 17, 2005, Inventor: Tomi Meilahti (which patent application is specifically referred to in applicant's specification [p. 6] herein), said application being attached hereto.

(Continued)

*Primary Examiner*—Edward J Glick
*Assistant Examiner*—Thomas R Artman
(74) *Attorney, Agent, or Firm*—Wood, Phillips, Katz Clark & Mortimer

(57) ABSTRACT

An X-ray source (101) is configured to controllably irradiate a sample (105) with incident X-rays through a sample window (104) that has a two-dimensional area. A detector (102) is configured to detect fluorescent radiation coming from the irradiated sample. A carrier (301, 401, 402, 501, 601) is essentially transparent to X-rays and disposed to spatially coincide with a substantial part of the two-dimensional area of the sample window (104). Marker material (303, 403, 602), which is responsive to X-rays by emitting fluorescent radiation, is mechanically supported by said carrier and essentially evenly distributed across at least that part of the carrier that spatially coincides with said two-dimensional area of the sample window.

17 Claims, 3 Drawing Sheets

U.S. PATENT DOCUMENTS

| | | | |
|---|---|---|---|
| 5,206,174 A | | 4/1993 | Gehrke et al. |
| 5,365,563 A | * | 11/1994 | Kira et al. ................ 378/48 |
| 5,578,360 A | | 11/1996 | Viitanen |
| 6,012,325 A | * | 1/2000 | Ma ........................ 73/24.02 |
| 6,043,486 A | * | 3/2000 | Hossain ................. 250/252.1 |
| 7,016,462 B1 | * | 3/2006 | Keville et al. ............. 378/47 |
| 2007/0111617 A1 | * | 5/2007 | Meilahti ..................... 442/1 |

FOREIGN PATENT DOCUMENTS

JP   5-312698   11/1993

OTHER PUBLICATIONS

European Search Report, EP 07118463.4-2204, Aug. 2, 2008, 6 pages.

* cited by examiner

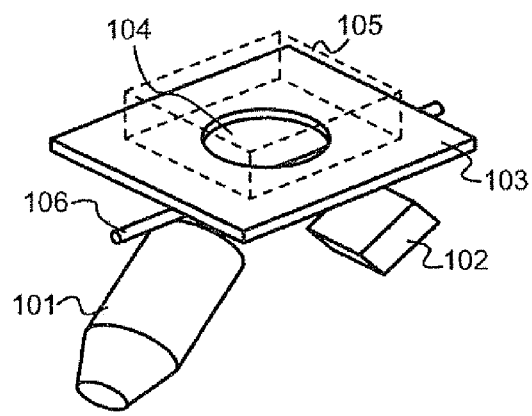
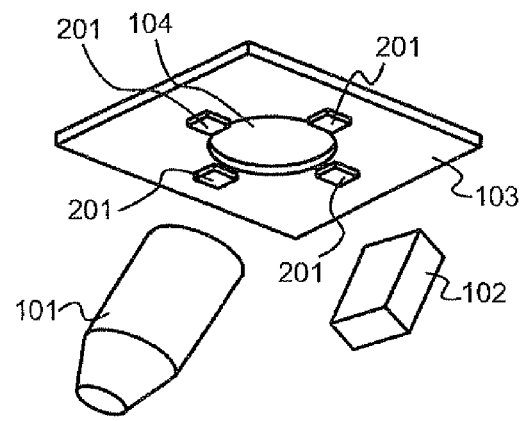
Fig. 1
PRIOR ART
Fig. 2
PRIOR ART
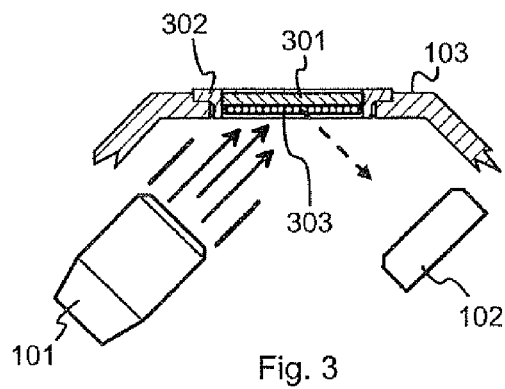
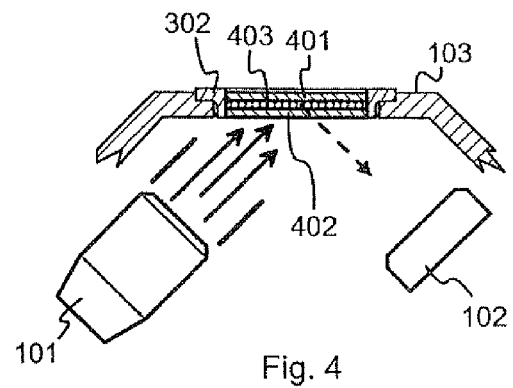
Fig. 3
Fig. 4
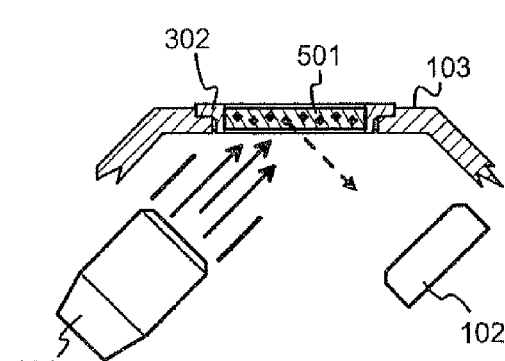
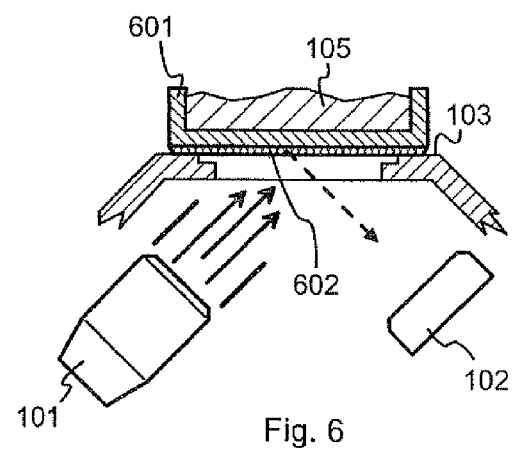
Fig. 5
Fig. 6

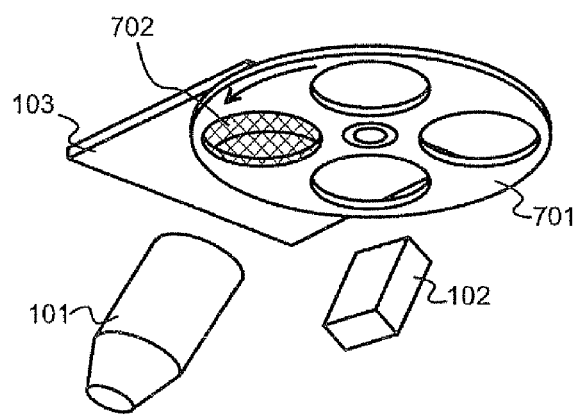
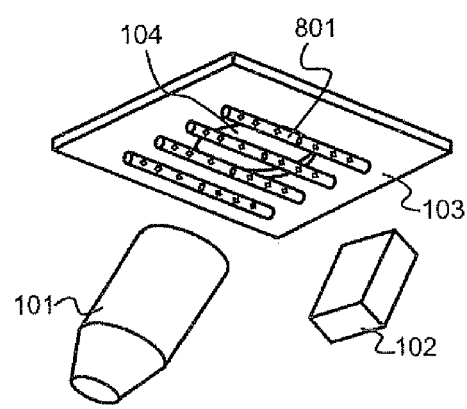
Fig. 7  Fig. 8
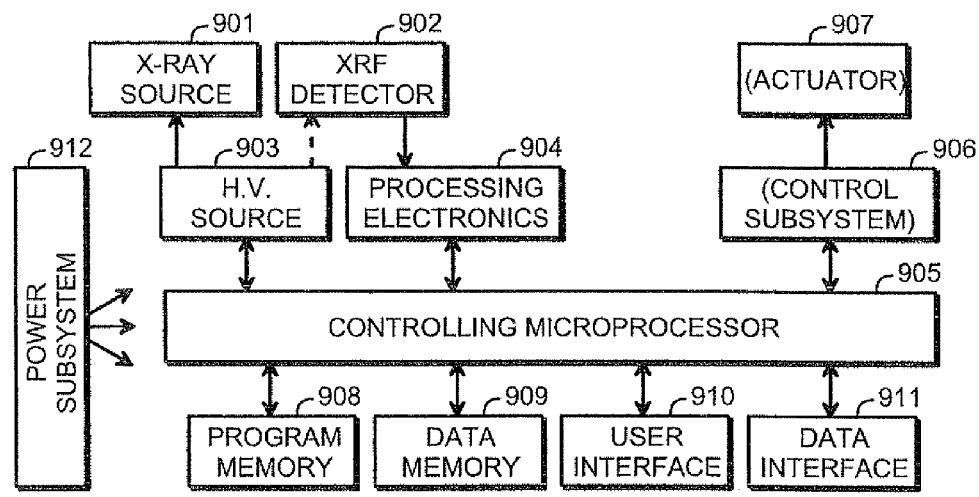
Fig. 9

COMPENSATION FOR FLUCTUATIONS OVER TIME IN THE RADIATION CHARACTERISTICS OF THE X-RAY SOURCE IN AN XRF ANALYSER

TECHNICAL FIELD

This invention concerns generally the technology of X-ray fluorescence (XRF) analyzers. Especially the invention concerns a method and an arrangement for making the analysis results less dependent on fluctuations in the radiation characteristics of the X-ray source.

BACKGROUND OF THE INVENTION

X-ray fluorescence analysis is a well-known method for investigating the material composition of a sample. X-rays from an X-ray source are allowed to irradiate the sample, which causes atoms of the sample constituents emit fluorescent radiation at characteristic energies. A detector receives the fluorescent radiation. By following the output of the detector it is possible to derive the spectral intensity of the fluorescent radiation. The relative numbers of received fluorescent photons at different energies reveal the proportions of different elements present in the sample.

In some X-ray fluorescence measurements it is important to know the absolute intensity of the incident X-rays that irradiate the sample. This is especially true when measuring soil or polymer samples, or other kinds of samples characterised by relatively low concentrations of heavy elements that are of interest, embedded in a matrix that consists of light elements. Since most practical X-ray fluorescence analysers use an X-ray tube as the source of incident radiation, the most straightforward way of finding out the absolute intensity is to make calibration measurements with known samples and to ensure that the X-ray tube will always be used under the same operating conditions (especially input voltage and current) as in calibration.

The generation of X-rays in an X-ray tube is fundamentally a stochastic process that involves a certain degree of statistic fluctuations. Additionally the electric circuit elements, however meticulously designed and controlled, that feed the input voltage and current to the X-ray tube, are inherently imperfect, which adds an unknown factor to the intensity fluctuations of the X-ray tube. It is also typical that after an X-ray tube has been switched on, it will take some time before the radiation intensity stabilizes to the value that has been observed in calibration measurements. This is a disadvantage concerning such XRF measurements that otherwise could be performed in a shorter time.

FIG. 1 illustrates schematically a known solution that enables monitoring dynamically the intensity of the incident radiation. An XRF analyzer comprises an X-ray tube 101, a detector 102 and a front plate 103. The device must have a solid outer cover that encloses all radiating parts, but here only the front plate is shown to better illustrate the concept. The front plate 103 defines a sample window 104, against which a sample 105 is to be placed. Radiation from the X-ray tube 101 irradiates the sample 105 through the sample window 104, and fluorescent radiation is measured with the detector 102. There is a thin wire 106 drawn across the empty space between the X-ray tube 101, the detector 102 and the sample window 104. The wire 106 is made of a material the X-ray fluorescence characteristics of which are well known. Fluorescent peaks of the wire material do not overlap with those of typical target materials. Some of the incident X-rays will hit the wire 106 and cause fluorescence in the atoms of the wire material. While measuring the fluorescence spectrum of the sample, the detector 102 also monitors the amount of fluorescent radiation coming from the wire 106. Since all other factors related to the fluorescence measurement of the wire 106 are constant, changes in the fluorescent radiation coming from the wire can only be caused by fluctuations in the intensity of incident radiation.

FIG. 2 illustrates schematically an alternative prior art solution. Here the front part of an X-ray analyzer device is seen from inside. The X-ray tube 101, the detector 102, the front plate 103 and the sample window 104 are similar to those in FIG. 1. Detectors 201 are located at the edges of the sample window 104. The intensity of the incident radiation is monitored directly by measuring that part of it that hits the detectors 201.

The solutions of FIGS. 1 and 2 share the inherent disadvantage that although they partly help to combat the overall intensity fluctuations over time, they do not take into account any spatial fluctuations in the X-ray beam. If a detector screen would be placed transversely across the X-rays emitted by the X-ray tube towards the sample window, and the two-dimensional intensity pattern detected by such a detector screen would be monitored, it would not be constant but would exhibit significant variation over time. As a specific example, we can imagine that at some times there may be a clear intensity maximum at the very center of the beam, whereas at some other time the intensity may be more evenly distributed or even have arbitrary peaks at the fringe areas. How accurately the solutions of FIGS. 1 and 2 will respond to such spatial fluctuations will depend heavily on how the spatial elements involved (the wire in FIG. 1, or the detectors in FIG. 2) will coincide with the arbitrarily located intensity maxima and minima across the beam.

An objective of the present invention is to present a method and an arrangement for dynamically compensating for variations in the intensity of incident radiation in an X-ray fluorescence analyzer, avoiding the drawbacks of prior art solutions.

The objectives of the invention are achieved by using material essentially transparent to X-rays to support a very small amount of marker material distributed across an area through which the incident radiation passes.

An analyzer device according to the invention includes a carrier that is essentially transparent to X-rays and disposed to spatially coincide with an essential part of the two-dimensional area of the sample window, and marker material responsive to X-rays by emitting fluorescent radiation, wherein said marker material is mechanically supported by said carrier and essentially evenly distributed across at least that part of the carrier that spatially coincides with the two-dimensional area of the sample window.

An analyzer arrangement according to the invention comprises a carrier, at least a part of which is essentially transparent to X-rays, and marker material responsive to X-rays by emitting fluorescent radiation. The carrier is movable to a first location in which at least a portion of said part of said carrier spatially coincides with an essential part of the two-dimensional area of the sample window. The marker material is mechanically supported by said carrier and essentially evenly distributed across at least that portion of the part of the carrier that in said first location spatially coincides with said two-dimensional area of the sample window.

The invention is also directed to a measurement method, which comprises:
  placing marker material, which is responsive to X-rays by emitting fluorescent radiation, so that the marker material is between an X-ray source and a sample and also between the sample and a detector and distributed essentially evenly across a substantial part of the two-dimensional area of a sample window that separates the sample from said X-ray source and said detector;
  using said X-ray source to irradiate the sample with incident X-rays through the sample window;

receiving fluorescent radiation from the irradiated sample and from the marker material with said detector and measuring the intensity spectrum of the received fluorescent radiation;

using the measured intensity spectrum to determine a correction factor, which comprises at least one of:

an indicator of the intensity of fluorescent radiation received from the marker material, and an indicator of the location of a fluorescent radiation peak from the marker material on an energy channel; and using said correction factor to process the measured intensity spectrum of fluorescent radiation received from the sample, thus producing a corrected intensity spectrum.

The idea of placing some marker material to the beam of incident radiation, like the wire used in some prior art solutions, is good as such. However, one should note that all such analyzer capacity, which is used to detect fluorescent radiation coming from the marker material, chips away at the useful capacity that is available for detecting actual fluorescence from the irradiated sample. Thus it would not be viable to add more wires to such a known solution to increase spatial coverage, because each wire must have a certain finite thickness in order to avoid breaking, and the overall amount of marker material in the beam would quickly become excessive.

However, the amount of marker material does not need to be very large if the marker material does not need to mechanically support itself. If some other material that is essentially transparent to X-rays is used as the mechanical support, it suffices to coat and/or dope the carrier material with such a small amount of marker material that even an essentially even distribution of marker material can by achieved across the whole area through which incident radiation passes to the sample.

The mechanical support for the marker material is most advantageously a window foil in the sample window, but also other possibilities exist.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF DRAWINGS

FIG. 1 illustrates a prior art arrangement for compensating for fluctuations in incident radiation, FIG. 2 illustrates another prior art arrangement for compensating for fluctuations in incident radiation, FIG. 3 illustrates a coated window foil in a sample window, FIG. 4 illustrates a layered sample window, FIG. 5 illustrates a doped sample window, FIG. 6 illustrates the use of a sample cup with a coated bottom, FIG. 7 illustrates an arrangement for changing filters in an analyzer device, FIG. 8 illustrates the use of marker-doped wires, FIG. 9 illustrates an analyzer device according to an embodiment of the invention.

DETAILED DESCRIPTION OF THE INVENTION

Figure 10:
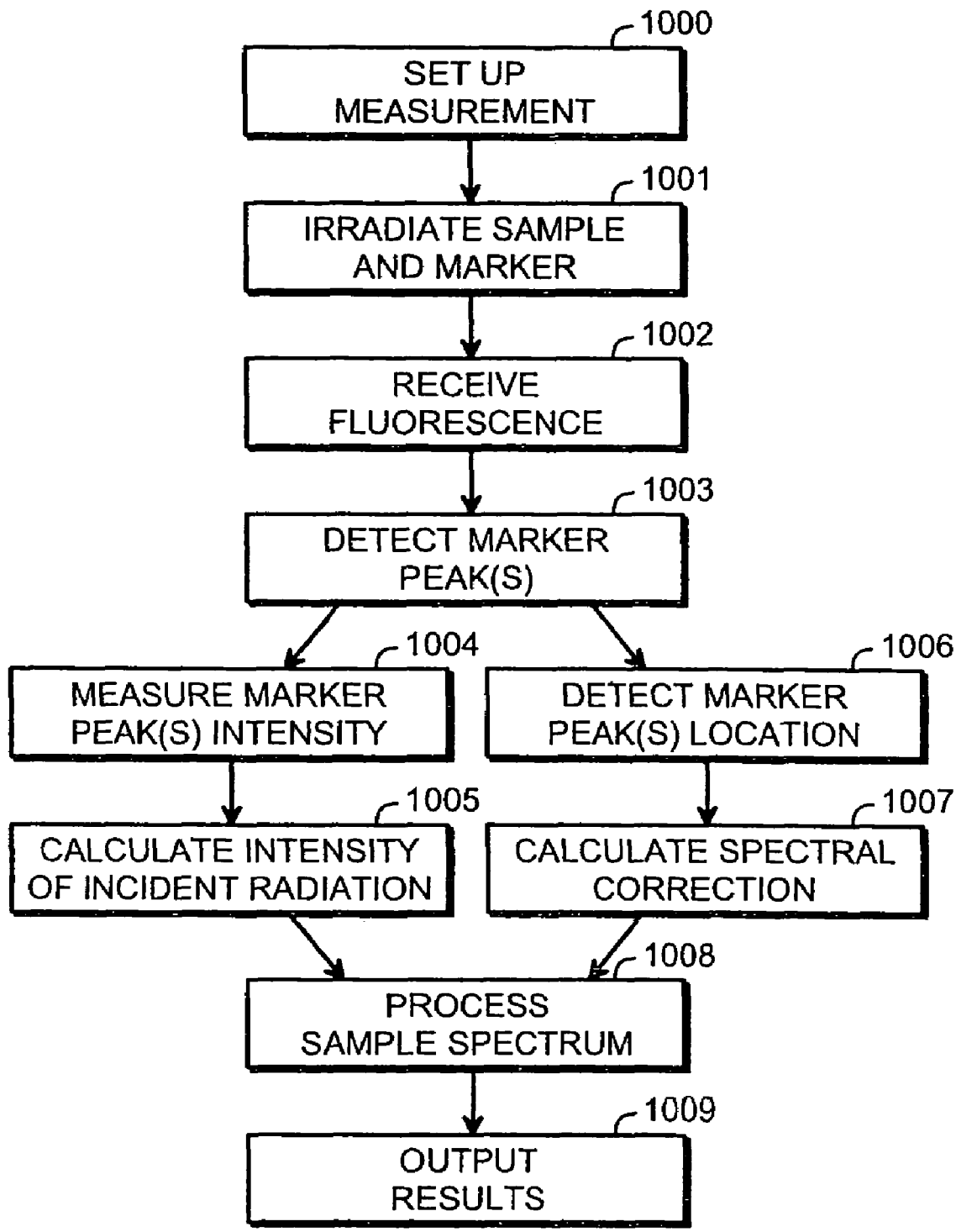
FIG. 10 illustrates a method according to an embodiment of the invention.

FIG. 3 illustrates schematically a front end of an XRF analyzer device. The term "front end" is conventionally used to designate that part of the analyzer device that incorporates the X-ray source 101 and the detector 102, and that comprises a part of the outer cover known as the front plate 103 that is configured to come against a sample for performing the XRF measurement. The front plate 103 defines a sample window for the incident X-rays and the fluorescent X-rays to pass through.

In the embodiment of FIG. 3 a protective window foil 301 is attached to the edges of the sample window with the help of a frame 302. The bulk of the window foil 301 is made of a material that is essentially transparent to X-rays, like diamond, beryllium or a plastic like polyimide. The role of the window foil 301 is basically to protect the inside of the analyzer device from contamination. If a particular gas atmosphere, lowered pressure, or other kind of controlled conditions are maintained inside the front end that differ from the ambient conditions, the window foil 301 is also needed to cover the sample window so that a closed space is formed. Radiation-permeable window materials suitable for this purpose are known for example from U.S. Pat. Nos. 5,578,360, 5,039,203, 4,119,234, 4,061,944, 3,319,064, 3,262,002, and 2,241,432, as well as from a co-pending U.S. patent application Ser. No. 11/281638 of the present applicant, which is incorporated herein by reference.

According to an embodiment of the invention there is an essentially even layer 303 of a marker material on a surface (here: inner surface) of the window foil 301. As a marker material, an element or a compound has been selected that has well-known X-ray fluorescence characteristics, and that is assumed to be seldom encountered in actual samples to be measured. An exemplary marker material is zirconium, but other materials could be used as well. The thickness of the marker material layer 303 is typically between 20 and 150 nanometers, depending somewhat on the selected marker material, the intensity of incident radiation that is going to be used, and the sensitivity of the detector and signal processing electronics. With zirconium as the marker material and with X-ray tubes, detectors and processing electronics typically encountered in hand-held XRF analyzers, the thickness of the layer 303 could be for example 50 nanometers. A zirconium layer that thin and large enough to cover a sample window would fall a way short of any capability of supporting itself, but it does not need to support itself either because the window foil 301 acts as a mechanical support.

The evenness of the layer 303 across the whole area of the sample window ensures that even if there are spatial and/or temporal fluctuations in the intensity of the incident X-ray beam, the radiation intensity that hits the marker material is always the same as the radiation intensity that hits the sample, except for attenuation in the window foil 301 and the marker material layer 303, which however is small and can be compensated for by simply multiplying the number of received fluorescent photons with an appropriate factor.

The arrangement of FIG. 3 is not the only possible way of arranging a support that is transparent to X-rays and using it to evenly distribute a small amount of marker material across a significant portion of the cross-section of the beam of incident X-rays. As the most straightforward example, it is not necessary to have the marker material layer on the inner surface of the window foil; the order of layers 301 and 303 could be switched in FIG. 3 so that the marker material would be on the outer surface of the foil. FIG. 4 illustrates a layered sample window foil that has two layers 401 and 402 that are transparent to X-rays and a marker material layer 403 between them. In layered window foil structures the marker material can be placed in any location in the order of layers. One could also use two or more marker material layers, at any locations in the order of layers, that may contain the same marker material or different marker materials.

It is not necessary to have the marker material in a separate layer different from the support layer. FIG. 5 illustrates an exemplary embodiment of the invention where a window foil 501 is basically made of a material transparent to X-rays but doped with a small amount of marker material, so that an essentially even distribution of marker material throughout the bulk of the window foil 501 is obtained. Here also the material that is transparent to X-rays acts as the mechanical support, because the amount of the marker material dopant is so small that it has a negligible effect on the mechanical strength of the window foil.

FIG. 6 illustrates a slightly different approach, in which the sample 105 is not placed directly against the front plate 103 but placed in a sample cup 601, at least the bottom part of which is made of a material transparent to X-rays. When the sample cup is in place adjacent to the front plate of the analyzer, a portion of the bottom part spatially coincides with the two-dimensional area of the sample window. Alternatively the sample cup may have a sample cup window at the bottom of the sample cup in a location that is to spatially coincide with the two-dimensional area of the sample window. The sample cup window is a portion transparent to X-rays. In that case the rest of the sample cup does not need to be transparent to X-rays. When a sample cup is used, it is not that important whether the sample window has a window foil to cover it or not. Here the sample window is shown as an opening without any window foil.

According to an embodiment of the invention, there is a marker material layer 602 on one surface of the sample cup 601. In the example of FIG. 6 the marker material layer 602 covers essentially the whole bottom surface of the sample cup 601, but—especially with sample cups that only have a limited portion made of a material transparent to X-rays—it is also possible that only a part of the bottom surface would be covered with the marker material. And as was discussed above concerning the various ways of using marker material in a sample window, all kinds of structural variations are possible, including but not being limited to having the marker material layer on the inner bottom surface of the sample cup, making the marker material appear as one or more layers in a layered structure of a (part of a) sample cup, and doping at least a part of the sample cup material with marker material.

FIG. 7 illustrates schematically a front end of an XRF analyzer device seen from inside. This analyzer device comprises a movable part 701, with which a user can select among a number of different kinds of foils to be placed in the space at the edges of which are the X-ray tube 101, the detector 102 and the front plate 103. In this exemplary schematic case the movable part 701 is illustrated as a disc that can be rotated around a central axis and that has openings across which the various foils have been drawn. Alternative ways of providing a comparable movable part are readily available: for example, there could be mechanisms for back-and-forth movement or one or more flaps configured to flip between a use position and a storage position. A movable part may comprise more than one foil like in the arrangement of FIG. 7, or there may be a separate movable part for each foil. Since the sample window typically comprises a separate protective window foil, it is advisable to design the movable mechanisms so that all additional foils can also be removed from the radiation path (for example so that one of the four openings in the movable part 701 does not have a foil at all).

Movable parts like that 701 in FIG. 7 can be manually movable or the analyzer may comprise the necessary means for electromechanically moving the appropriate movable parts as a response to commands given by a user.

The movable part(s) can be used to selectively place filters across the radiation path as required. According to an embodiment of the present invention, at least one opening in the movable part 701 of FIG. 7 comprises a marker material foil 702, which has a radiation-transparent mechanical carrier layer and a thin layer of marker material. Structurally the marker material foil 702 may resemble any of the foil structures that have been discussed above with reference to FIGS. 3, 4, and 5. The marker material foil 702 can simultaneously have other kinds of filtering functions, or it may be provided simply for the purpose of using the marker material only. It is also possible that more than one of the foils that can be selectively placed across the radiation beam carry marker material; such multiple marker material foils can all have the same marker material characteristics or they may carry e.g. different marker materials or different amounts of the same marker material.

FIG. 8 illustrates a yet another embodiment of the invention, which utilizes the fact that the mechanical carrier material is essentially transparent to X-rays. In this embodiment there is no continuous marker material foil, but a number of wires 801 have been drawn across the the space at the edges of which are the X-ray tube 101, the detector 102 and the front plate 103. The bulk material of the wires 801 is transparent to X-rays and acts as the mechanical carrier, but the wires have a very thin plating or a small amount of doping made of a marker material.

The embodiment of FIG. 8 is inferior to those embodiments of the invention that rely on a continuous carrier layer and the consequently continuous, even distribution of marker material across the whole area through which irradiation of the sample takes place, because in FIG. 8 there are areas between the wires where the incident radiation will not encounter any marker material. Fluctuations in intensity will thus go unnoticed if they only happen to occur on those areas. However, FIG. 8 serves to illustrate the fact that the invention does not place an absolute requirement of having marker material coincide with the whole two-dimensional area of the sample window. In order to compensate for fluctuations, it is sufficient that marker material (and its transparent carrier) spatially coincides with a substantial part of the two-dimensional area of the sample window. What is sufficient in this respect depends on the accuracy that is aimed at. In applications where it is truly important to detect even minor fluctuations in incident radiation intensity, indepently of where in the beam they occur, it may become essential to make marker material (and its transparent carrier) exactly coincide with the whole two-dimensional area of the sample window.

FIG. 9 illustrates schematically some functional blocks of an analyzer device according to an embodiment of the invention. The X-ray source 901 is selected so that the incident X-rays it produces will be useful in exciting not only the desired sample atoms but also those of the marker material. The X-ray detector 902 is selected so that it can reliably detect also the fluorescent radiation coming from the marker material. A high voltage source 903 is coupled to deliver the necessary high voltages at least to the X-ray source 901 and possibly also to the X-ray detector 902, if high voltages are needed there for biasing.

The output signals of the X-ray detector 902 are coupled to a processing electronics block 904, which is configured to implement signal processing functions such as amplification, pulse shaping, filtering and A/D conversion.

If there are electromechanically movable parts in the analyzer device, it it advantageous to have an actuator 907 configured to move the movable part(s) under the command of a control subsystem 906, which in turn is coupled to receive instructions from a controlling microprosessor 905.

The controlling microprocessor 905 is configured to act as the central controlling entity of the XRF analyzer. It controls the operation of the high voltage source 903 and possibly receives feedback therefrom; it receives the measurement information from the processing electronics block 904 and tunes the signal processing operations if needed; and it gives the control commands to the control subsystem 906, if any is present, and receives feedback. The controlling microprocessor 905 operates by executing a program stored in a program memory 908 and uses a data memory 909 for storing and retrieving data. The controlling microprocessor 905 is also coupled to a user interface 910, which typically comprises keys and/or switches through which a user can give input commands, and a display and/or other sensory indicators, such as lights and buzzers, to give sensory feedback to the user. A data interface 911 is provided and coupled to the controlling microprocessor 905 so that the XRF analyzer may exchange data with other electronic devices. The functionalities that are described here to take place in a single controlling microprocessor 905 may, in a way well known as such, be distributed among a number of different parts or circuits of the XRF analyzer. A conventional power subsystem 912 is configured to feed operating power to all electrically driven parts of the XRF analyzer.

According to an embodiment of the invention the controlling microprocessor 905 is configured to detect the intensity of fluorescence coming from the marker material and to derive from it the momentary intensity of the incident radiation. Several practical ways of implementing such functionality exist. For example, a part of the program memory 908 may comprise a look-up table, in which there have been stored a number of incident radiation intensity values and their correspondence with intensity values for fluorescence radiation coming from the marker material. Another possibility is to store in the program memory a mathematical formula, into which the controlling microprocessor 905 may insert any obtained intensity intensity value for fluorescence radiation coming from the marker material, and calculate the corresponding intensity of incident radiation.

The system level configuration of FIG. 9 is applicable irrespective of whether the XRF analyzer is of a portable, hand-held type or of a benchtop type. In portable devices small size and weight are important design drivers, and power consumption should be minimized because the power subsystem 912 relies on rechargeable batteries for wireless operation. In benchtop devices size and weight are less of a concern, which may allow e.g. the use of more versatile selections of movable parts and corresponding different filter and foil arrangements (see FIG. 7).

The analyzer device implements the so-called multichannel analysis principle, which means that the energy of each fluorescent photon hitting the detector is only measured accurately enough to take it into account as a count in the appropriate, narrow energy range or channel. The measured intensity spectrum is synonymous to the collection of accumulated counts on each channel over a given time. Based on calibration, in principle the analyzer device knows the correspondence between photon energies and channels. However, there are always error sources that cause for example an unexpected constant shift k, so that a detected photon with energy E is not counted in channel n as it should but in channel n+k instead. More complicated errors in the correspondence between photon energies and channels may include for example a linearly varying shift, so that a detected photon with energy E that should be counted in the n:th channel is counted in the channel number n+(a+bn) instead.

The energy spectrum of the characteristic fluorescent radiation emitted by the marker material is known beforehand, and typically exhibits a clear peak that should coincide with a particular channel. If the controlling microprocessor 905 is programmed to detect the fluorescent peak of the marker material in the measured energy spectrum, and to note the possible shift between the channel at which the peak is detected and the channel at which it should be, it can use said shift as an indication of what kind of correction(s) it should make to other parts of the measured energy spectrum in order to compensate for the errors that caused the shift.

"Online calibration" of the kind referred to above can be made even more versatile if there are more than one fluorescent peak from the marker material(s) available in the measured energy spectrum, or if the observed shift of the marker material peak(s) can be combined to observed shifts of other peaks in the measured spectrum, coming from sample materials that are believed to be reliably recognized. For a person skilled in the art it is easy to present mathematical formulas for correcting measured spectra based on observed shifts of peaks at various locations in the spectrum.

FIG. 10 illustrates schematically a method according to an embodiment of the invention. Step 1000 refers generally to setting up the measurement arrangement, including e.g. placing the sample appropriately and—especially if the marker material is on a movable carrier—placing marker material so that the marker material is between an X-ray source and a sample and also between the sample and a detector, and distributed essentially evenly across a substantial part of the two-dimensional area of a sample window that separates the sample from the X-ray source and the detector.

At step 1001 the sample is irradiated with incident radiation; at the same time some of the incident radiation also hits the marker material. At step 1002 the fluorescent radiation from both the sample and the marker material is received. At step 1003 the energy spectrum of the received fluorescent radiation is examined in order to find at least one characteristic peak coming from the marker material. Since the marker material has been selected so that its characteristic fluorescent peaks do not overlap with significant peaks from typical sample constituents, and since the energy of said characteristic fluorescent peaks is known, step 1003 may mean in practice for example that each marker peak that is to be used is first sought in the energy channel where it should be in the absence of error sources, and then on adjacent channels on both sides of that channel going progressively further away from the original channel until the peak is found.

Steps 1004 and 1005 relate to using marker fluorescence to compensate for fluctuations in intensity of the incident radiation. Steps 1006 and 1007 relate to using marker fluorescence to compensate for unexpected shifts in the correspondence between photon energies and channels. The method may comprise any combination of steps 1004-1005 with steps 1006-1007, including but not being limited to only performing steps 1004-1005 but not steps 1006-1007, only performing steps 1006-1007 but not steps 1004-1005, and performing steps 1004-1005 more often or less often than steps 1006-1007.

Step 1004 means measuring the intensity of the detected fluorescence from the marker material, and step 1005 means using the measured marker fluorescence intensity to derive an indicator of the corresponding intensity of incident radiation. Step 1006 means detecting, at which channel(s) the marker fluorescence peak(s) occur, and step 1006 means using the detected peak's location or the detected peaks' locations to derive one or more indicators of how should the measured fluorescence spectrum from the sample be processed in order to restore the correct correspondence between photon energies and channels.

At step 1008 the measured spectrum of the fluorescence coming from the sample is processed using at least one of the indicators obtained from at least one of steps 1005 and 1007. At step 1009 the results are output.

We claim:

1. An X-ray fluorescence analyzer device, comprising:
   an X-ray source configured to controllably irradiate a sample with incident X-rays through a sample window that has a two-dimensional area,
   a detector configured to detect fluorescent radiation coming from the irradiated sample,
   a carrier foil that is essentially transparent to X-rays and disposed to spatially coincide with a substantial part of the two-dimensional area of the sample window, and
   marker material responsive to X-rays by emitting fluorescent radiation,
   wherein said marker material is mechanically supported by said carrier and essentially evenly distributed across at least that part of the carrier that spatially coincides with said two-dimensional area of the sample window.

2. A device according to claim 1, wherein:
   the device comprises a front plate,
   said sample window is an opening in said front plate, and
   said carrier is a foil that closes said opening.

3. A device according to claim 2, wherein the marker material exists as a layer on a surface of said foil.

4. A device according to claim 3, wherein the marker material is on that surface of said foil that is towards the inside of the analyzer device.

5. A device according to claim 2, wherein said foil comprises at least two layers of material essentially transparent to X-rays, and the marker material is between said two layers.

6. A device according to claim 2, wherein the marker material is a dopant embedded in a bulk material of said foil.

7. A device according to claim 1, wherein:
   the device comprises a front plate,
   said sample window is an opening in said front plate, and
   said carrier is a foil disposed in the space between the X-ray source, the detector and the front plate.

8. A device according to claim 7, comprising a movable part configured to allow said foil to be moved between a first location in which said foil coincides with an essential part of the two-dimensional area of the sample window and a second location in which said foil does not coincide with any essential part of the two-dimensional area of the sample window.

9. A device according to claim 8, wherein said movable part defines a multitude of openings, each of which is movable in its turn to a location in which it coincides with an essential part of the two-dimensional area of the sample window, and wherein said foil closes one of said multitude of openings.

10. An X-ray fluorescence analyzer arrangement, comprising:
    an X-ray source configured to controllably irradiate a sample with incident X-rays through a sample window that has a two-dimensional area,
    a detector configured to detect fluorescent radiation coming from the irradiated sample,
    a carrier foil, at least a part of which is essentially transparent to X-rays, and
    marker material responsive to X-rays by emitting fluorescent radiation,
    wherein:
    said carrier foil is movable to a first location in which at least a portion of said part of said carrier spatially coincides with an essential part of the two-dimensional area of the sample window,
    said marker material is mechanically supported by said carrier and essentially evenly distributed across at least that portion of the part of the carrier that in said first location spatially coincides with said two-dimensional area of the sample window.

11. An arrangement according to claim 10, wherein said carrier is a sample cup configured to hold the sample during an X-ray fluorescence measurement of the sample.

12. An arrangement according to claim 11, wherein a bottom part of the sample cup comprises a sample cup window, which is a foil essentially transparent to X-rays, and the marker material exists as a layer on a surface of said foil.

13. An arrangement according to claim 10, wherein said carrier is a movable part configured to allow a foil to be moved between a first location in which said foil coincides with an essential part of the two-dimensional area of the sample window and a second location in which said foil does not coincide with any essential part of the two-dimensional area of the sample window, and the marker material exists as a layer on a surface of said foil.

14. An arrangement according to claim 13, wherein said movable part is located at least partly inside a housing that also houses the X-ray source and the detector.

15. A method for compensating for errors in an X-ray fluorescence measurement, comprising:
    placing marker material, which is responsive to X-rays by emitting fluorescent radiation, so that the marker material is between an X-ray source and a sample and also between the sample and a detector and distributed essentially evenly across a substantial part of the two-dimensional area of a sample window that separates the sample from said X-ray source and said detector;
    using said X-ray source to irradiate the sample with incident X-rays through the sample window;
    receiving fluorescent radiation from the irradiated sample and from the marker material with said detector and measuring the intensity spectrum of the received fluorescent radiation;
    using the measured intensity spectrum to determine a correction factor, which comprises at least one of:
    an indicator of the intensity of fluorescent radiation received from the marker material, and
    an indicator of the location of a fluorescent radiation peak from the marker material on an energy channel; and
    using said correction factor to process the measured intensity spectrum of fluorescent radiation received from the sample, thus producing a corrected intensity spectrum.

16. A method according to claim 15, wherein using said correction factor to process the measured intensity spectrum comprises scaling measured intensities on energy channels on the basis of the indicator of the intensity of fluorescent radiation received from the marker material.

17. A method according to claim 15, wherein using said correction factor to process the measured intensity spectrum comprises restoring correspondences between fluorescent photon energies and energy channels on the basis of the indicator of the location of a fluorescent radiation peak from the marker material on an energy channel.

* * * * *